United States Patent [19]

Dang Vu et al.

[11] 4,270,929
[45] Jun. 2, 1981

[54] PROCESS FOR PRODUCING GASOLINE OF HIGH OCTANE NUMBER, IN PARTICULAR LEAD-FREE GASOLINE

[75] Inventors: Quang Dang Vu, Paris; Yves Chauvin, Le Pecq; Jean Gaillard, Lyons; Bernard Torck, Boulogne sur Seine; Michel Hellin, Andresy, all of France

[73] Assignee: Institut Francais du Petrole, Rueil-Malmaison, France

[21] Appl. No.: 71,503

[22] Filed: Aug. 31, 1979

[30] Foreign Application Priority Data

Aug. 31, 1978 [FR] France ................................ 78 25359

[51] Int. Cl.³ ............................................. C10L 1/02
[52] U.S. Cl. ............................................ 44/56; 585/3; 585/14
[58] Field of Search .................... 585/302, 2, 3, 14; 44/56

[56] References Cited

U.S. PATENT DOCUMENTS 2,403,869  7/1946  Marschner ........................... 585/302
3,912,463  10/1975  Kozlowski et al. ....................... 44/56

OTHER PUBLICATIONS

Reynolds et al., "Methyl Ether (MTBE) Scores Well as High-Octane Gasoline Component", The Oil and Gas Journal, Jun. 16, 1975, vol. 73, 1975, pp. 50–52.

Primary Examiner—Winston A. Douglas
Assistant Examiner—Y. Harris-Smith
Attorney, Agent, or Firm—Millen & White

[57] ABSTRACT

Process for producing gasoline of high octane number from $C_3$ and $C_4$ olefinic cuts, such as those obtained by fractional distillation of a $C_3/C_4$ catalytic cracking cut, comprising the steps of:
(a) oligomerizing propylene of the $C_3$ cut to obtain a first gasoline fraction,
(b) reacting the isobutene of the $C_4$ cut with methanol to produce methyl tert.-butyl ether which is separated from the unreacted $C_4$ hydrocarbons to form a second gasoline fraction,
(c) alkylating said unreacted $C_4$ hydrocarbons with isobutane in the presence of an alkylation catalyst such as hydrofluoric acid, to form a third gasoline fraction, and
(d) admixing, at least partially, said first, second and third gasoline fractions, so as to obtain gasoline of high octane number.

9 Claims, 1 Drawing Figure

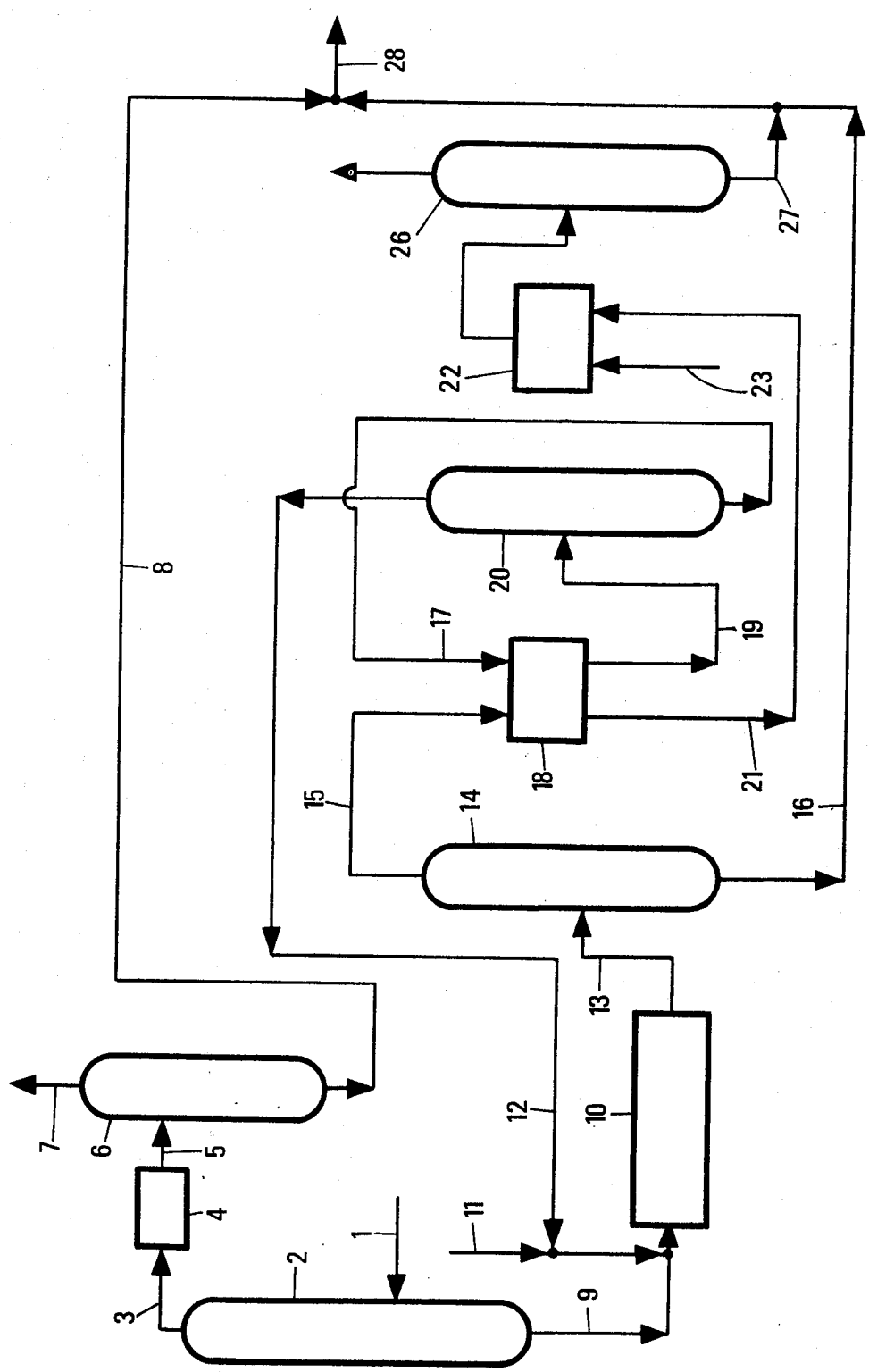

PROCESS FOR PRODUCING GASOLINE OF HIGH OCTANE NUMBER, IN PARTICULAR LEAD-FREE GASOLINE

BACKGROUND OF THE INVENTION

This invention concerns a process for producing gasoline or a gasoline component of high octane number which may be used without addition of an antiknock agent such as tetraethyl lead.

THE PROBLEM

Up to now lead-free gasoline was mainly produced by:
Very severe catalytic reforming of naphtha, or
Alkylation with isobutane of $C_3$–$C_4$ catalytic cracking cuts containing olefins.

Lead-free gasoline, produced by catalytic reforming of high severity, is not ideal with respect to pollution and public health. As a matter of fact it contains benzene, whose vapor has proved very toxic.

On the contrary, alkylation yields gasoline which is satisfactory as concerns both the ecological point of view and the purely technical engine problems.

Unhappily this route is essentially restrained by the isobutane shortage.

More than ever it is necessary to find a process to obtain valuable products from olefinic $C_3$–$C_4$ cuts, which process is self-sufficient in isobutane and capable to produce gasoline of equivalent quality.

The reaction between isobutane and a $C_3$ or $C_4$ olefin being equimolecular, it has been calculated that the required theoretical amount of isobutane is 1.38 kg for 1 kg of propylene and 1.035 kg for 1 kg of butenes.

It has been observed that the $C_3$–$C_4$ catalytic cracking cuts suffer generally from the drawback of a heavy lack of balance with respect to the isobutane content which is far from being sufficient to satisfy the above stoichiometry. A typical cut has the following composition (% by weight):

| | |
|---|---|
| propene | 25.00 |
| propane | 8.35 |
| isobutane | 23.35 |
| isobutene | 10.65 |
| n. 1-butene | 6.65 |
| n. 2-butene | 18.00 |
| $nC_4$(n-butane) | 8.00 |

The above composition shows that the isobutane proportion is not even one third of the stoichiometrical proportion of olefins.

STATE OF THE ART

The lack of balance of $C_3$–$C_4$ cuts is well known. For example U.S. Pat. No. 3,758,628 proposes to obviate it by using simultaneously a hydrocracking unit and a catalytic cracking unit. But, as shown above, the present trend is towards a stagnation or even a reduction in the number and the capacity of the existing hydrocracking units. Moreover, hydrocracking is an expensive operation which produces numerous products other than isobutane, which are not always valuable.

During the last years, attempts have been made to mix alcohols, ethers, etc . . . , with gasoline, either to improve the octane number or to deal with the oil shortage, or for other purposes.

Such attempts have been described for example, in U.S. Pat. No. 3,726,942 and French Pat. No. 2,063,939.

It does not seem, however, that a really economical way of operation has been attained either as a result of a too high production cost or of insufficient gasoline performances.

THE INVENTION

The present invention resolves the above problem in a very new, simple and economical manner. One object of the invention is, instead of finding an additional external source of isobutane, to modify the composition of the $C_4$ cut so that said composition is closer to the stoichiometry of the alkylation reaction of olefins with isobutane.

Another object of the invention is to improve the quality of the alkylate by modifying the composition of butenes in such a manner that the resulting products have a better octane number. This is achieved by providing for the alkylation of $C_4$ olefins enriched with n-butenes and improverished or made free of propylene and isobutene. As a matter of fact, the alkylates obtained by reaction of isobutane with propylene or isobutene have an octane number which is not so high as those obtained by reacting isobutane with 2-butene; Research Octane Number: 92.7 when starting from isobutene, 96.8 and 96.2 respectively when starting from 1-butene and 2-butene and about 90 when starting from propylene.

It must be noted that these values correspond to a conventional alkylation with sulfuric acid.

In the case of an alkylation with hydrofluoric acid (HF), higher values can be obtained, i.e.:

91 for propylene, 95.9 for isobutene, 94.4 for 1-butene, 97.6 for cis 2-butene, 97.8 for trans 2-butene.

Another object of the invention is to obtain gasoline or a gasoline component of high octane number, which can be used without lead additive.

According to the invention, the $C_3$/$C_4$ hydrocarbon charge, when not available as separate $C_3$ and $C_4$ fractions, is fractionated to a first fraction (A) of high $C_3$ hydrocarbon content, particularly of high propylene content, and a second fraction (B) of high $C_4$ hydrocarbon content, particularly of high isobutane, isobutene, 1-butene and 2-butenes content.

The first fraction (A) is selectively oligomerized essentially to $C_6$ and $C_9$ olefinic hydrocarbons, with a major portion of $C_6$ olefinic hydrocarbons, to form a first fraction (I) of gasoline of high octane number (oligomerizate). The second fraction (B) is reacted with methanol, in the presence of an acid catalyst, so as to obtain methyl tert.-butyl ether by reaction of isobutene with methanol. The product of this reaction is fractionated so as to separate the unreacted hydrocarbons from the methyl tert.-butyl ether which consititutes the second fraction (II) of high octane number gasoline.

The unreacted hydrocarbons are those from fraction (B) with however a zero content or, at least, a decreased content of isobutene, due to the fact that the normal olefins substantially do not react with methanol. In this hydrocarbon mixture, as a result of the lowering of the isobutene content, the isobutane/olefin ratio is increased and approaches or attains the theoretical molar ratio of 1.

This mixture is then subjected to aliphatic alkylation either as such or after addition of isobutane, said addition being however much smaller than that which would have been made when omitting the step of etherification of isobutene. There is thus obtained an alkylate which constitutes the third fraction (III) of gasoline of high octane number.

The fractions I, II and III can then be mixed, partly or completely, in order to obtain a gasoline or a gasoline component of high octane number which can be used without lead, either as such or in admixture with, for example, a reformate or other fractions in the gasoline range.

It is possible, if so desired, to proceed to a stabilization of fractions I, II and III, either separately on each fraction or on their mixture.

DETAILED DESCRIPTION OF THE INVENTION

The hydrocarbon charge is preferably a $C_3$–$C_4$ catalytic cracking fraction. It may be available as a $C_3$–$C_4$ mixture and must then be fractionated to a $C_3$ fraction and a $C_4$ fraction as above-mentioned; it may also be available as separate $C_3$ and $C_4$ fractions, for example as obtained by distillation of the effluents from a catalytic cracking unit.

The catalytic cracking may be of any type, for example a fluid catalytic cracking fed with a distillate of high saturated hydrocarbon content produced, for example, by direct distillation of crude oils. The catalytic cracking processes are well known and a detailed description thereof is unnecessary. The catalysts are, for example, silica-alumina, a clay or a zeolite. A detailed description is given, for example, in U.S. Pat. No. 3,758,628.

The $C_3$–$C_4$ fraction usually contains from 0.15 to 0.6 mole of isobutane per mole of olefins. With this condition, a typical composition by weight is as follows:

| | |
|---|---|
| isobutane | 15 to 30% |
| propene | 15 to 35% |
| isobutene | 5 to 15% |
| 1-butene | 3 to 10% |
| 2-butenes | 10 to 25% |
| propane + n-butane | 8 to 30% |

When the product obtained by catalytic cracking is already in the form of separate $C_3$ and $C_4$ cuts, their composition is for example as follows (by weight):

| | | |
|---|---|---|
| $C_3$ cut | propane | 15–50% |
| | propylene | 50–85% |
| $C_4$ cut | n-butane | 5–20% |
| | isobutane | 20–50% |
| | isobutene | 10–25% |
| | 1-butene | 5–15% |
| | 2-butene | 10–40% |

The fractionation between $C_3$ and $C_4$ fractions is easy to achieve by distillation. It is not necessary that the $C_3$ fraction be entirely free of $C_4$ hydrocarbons nor that the $C_4$ fraction be entirely free of $C_3$ hydrocarbons.

The oligomerization of the $C_3$ hydrocarbon cut is preferably performed in the liquid phase by contacting said cut with a catalyst obtained by contacting (or reacting) a compound of a transition metal from groups IV to VIII with an alkylaluminum, preferably a compound of nickel with a hydrocarbylaluminum halide, for example a monohydrocarbylaluminum dihalide or a hydrocarbylaluminum sesquichloride. The reaction is conducted in most cases at a temperature from 0° to 60° C., preferably from 30° to 50° C. The nickel compound may, for example, consist of a carboxylate, an acetylacetonate, a phosphine complex of a nickel salt such as a chloride or an acetylacetonate. The reaction is well known and reference may be had, for example, to the following patent specifications: U.S. Pat. Nos. 2,969,408 and 3,655,810 and French Pat. No. 1,591,577. As state of the art, there will be mentioned U.S. Pat. Nos. 3,032,544; 3,390,201; 3,485,881; 3,321,546; 3,482,001 and 3,467,726.

Compounds of other metals than nickel may also be used, such as, for example, compounds of titanium (U.S. Pat. No. 3,686,350), cobalt (U.S. Pat. No. 3,686,353), chromium (U.S. Pat. Nos. 3,709,954 and 3,726,939), vanadium (U.S. Pat. No. 3,737,476), tungsten (U.S. Pat. No. 3,784,629), etc.

Preference is given to the combination of a nickel compound with a dichloroalkylaluminum, in view of its better selectivity to produce olefins with 6 carbon atoms.

When the oligomerization has been completed, there is obtained an oligomerizate (I) which constitutes one of the desired gasoline fractions.

Other oligomerization techniques may be used, such, for example, as the treatment with a catalyst of silica-alumina, phosphoric acid, boron trifluoride, aluminum trichloride, etc.

The results are however less satisfactory with respect to the composition of the oligomerizate which contains more of the heavier oligomers having 9, 12 and 15 carbon atoms; moreover the catalyst is difficult to handle, it must be changed frequently and it must be operated under relatively high pressure. The state of the art is given, for example, by U.S. Pat. Nos. 3,769,363; 3,833,678; 3,758,627 and 3,887,634.

The reaction between the isobutene of the $C_4$ cut and methanol is performed in the presence of an acid catalyst, for example sulfuric acid, hydrofluoric acid, aluminum chloride and boron fluoride. However, it is preferred to make use of carbonaceous materials containing —$SO_3H$ groups, for example sulfonated carbons (e.g. X or AX Nalcite, H ZeO-Karb), sulfonated phenol-formaldehyde resins (for example Amberlite IR-1 or IR-100, Nalcite MX), sulfonated coumaroneindene polymers or, preferably, sulfonated polystyrene-divinylbenzene resins, for example Dowex 50, Nalcite HCR and Amberlyst 15.

When proceeding in a continuous manner, the volume of charge treated per volume of catalyst and per hour is usually from 0.5 to 20. Usual operating conditions are a temperature from 20° to 150° C., preferably from 40° to 100° C., a proportion of 1 to 10 moles of methanol per mole of isobutene, an alcohol excess favouring the reaction.

The etherification reaction is well known and described for example in U.S. Pat. Nos. 2,480,940; 3,037,052 and 3,281,475.

The alkylation reaction is conducted under conventional conditions for aliphatic alkylation. The known catalysts for the reaction of isobutane with butenes may be used, hydrofluoric acid being preferred. Other catalysts are sulfuric acid, phosphoric acid or Friedel and Crafts catalysts.

As state of the art, there will be mentioned U.S. Pat. Nos. 2,308,560; 2,320,199; 2,429,205; 2,768,987; 2,818,458; 2,914,592; 2,920,124; 2,429,205 and 3,855,344, among others.

The invention is not limited to particular conditions of the well known alkylation reaction. There is thus obtained an alkylate (III) which constitutes the third gasoline fraction of high octane number and can be admixed with the oligomerizate (I) and the ether (II). Preferably at least 90% by weight of the final gasoline distils between 40° and 220° C.

The invention is illustrated by the accompanying drawing.

A catalytic cracking effluent (line 1) or preferably a $C_3$–$C_4$ fraction from said effluent is fractionated in a distillation unit diagrammatically shown as a column 2, into $C_3$ and $C_4$ fractions. The $C_3$ fraction is fed, through line 3, to the oligomerization unit 4. The effluent from said unit is supplied, through duct 5, to column 6 to be fractionated. The light hydrocarbons are separated through line 7; they may be recycled to unit 4. There is recovered an oligomerization gasoline fraction through line 8. Its distillation range is between about 40° and 220° C., but it mainly contains propylene dimers. This fraction is fed to the gasoline "pool."

The $C_4$ fraction, withdrawn from line 9, is supplied to the alkylation unit 10, fed with methanol through line 11. This methanol is partly supplied from the recycle duct 12. At the outlet of the alkylation unit, the product is conveyed through line 13 to the stabilization column 14. At the top (line 15) there are recovered unreacted $C_4$ hydrocarbons together with unconverted methanol; at the bottom there is recovered methyl tert.-butyl ether (line 16).

The $C_4$ cut may be subjected to water washing in order to remove therefrom at least a part of the unconverted methanol; the water is introduced through line 17 into the washer 18. By decantation, there is recovered an aqueous phase and a $C_4$ hydrocarbon phase. The aqueous phase is fed, through line 19, to the distillation column 20: methanol is recycled through line 12 and water may be fed back to the washing unit through line 17. The $C_4$ hydrocarbon phase is dried, if required, and fed through line 21 to the alkylation unit 22. Additional isobutane may be introduced, when necessary, through line 23. The alkylate is fed, through line 25, to the stabilization column 26. At the top thereof, there is essentially withdrawn n-butane and at the bottom the desired alkylate. The latter, discharged through line 27, may join the other gasoline fractions (lines 8 and 16) to provide a gasoline usable without lead (line 28).

EXAMPLE

The composition of the $C_3/C_4$ hydrocarbon charge and of the obtained fractions is given in the following Table. The operation has been conducted according to the diagram of the accompanying drawing.

The operating conditions were as follows:

First, the $C_3$ and $C_4$ hydrocarbons have been separated by distillation.

The propylene oligomerization unit was operated with a catalytst formed of nickel octoate and dichloroethylaluminum in an atomic ratio Al/Ni of 15:1 at a concentration of 20 parts per million by weight of nickel at a temperature of 40°–45° C., under a pressure sufficient to maintain propylene and propane in the liquid phase (about 10 bars) and with a total residence time of 3 hours. At the outlet of the reactor, the catalyst has been first neutralized with anhydrous ammonia and then washed with water to remove the catalyst residues. The effluent has then been fed to a stabilization column: at the top unreacted propane and propylene were recovered and at the bottom the stabilized oligomerizate.

The $C_4$ hydrocarbon fraction has been fed with methanol to an etherification reactor operating according to the following conditions:

Catalyst: ion exchange resin based on polystyrene cross-linked with divinylbenzene (Amberlyst 15)

Operating conditions:

| temperature | 50–90° C. |
|---|---|
| pressure | 10–20 bars |
| molar ratio methanol/isobutene | 1.02 |

The product is distilled and there is recovered at the top an azeotrope of residual $C_4$ hydrocarbon/methanol and at the bottom the methyl tert.-butyl ether (MTBE).

The residual $C_4$ cut is washed with water to recover unconverted methanol and then dried.

The washing aqueous phase is distilled to recover methanol which is recycled to the etherification reactor.

The residual $C_4$ cut, after washing and drying, is fed to the alkylation reactor, operated as follows:

Catalyst: hydrofluoric acid at 85.9% by weight.

Temperature: 27°–38° C.; pressure: 14 bars; molar ratio isobutane/olefins: 6/1

Counter-current reactor with recycling of unconverted isobutane.

After decantation, the organic phase is fractionated to give the alkylate and the isobutane to be recycled.

The alkylate has been fed to a stabilization column, in order to separate n-butane from the traces of residual isobutane. An alkylate is recovered which is admixed with the methyl tert.-butyl ether (MTBE) and the oligomerizate. The resultant mixture consists of a gasoline having a research octane number (RON) without lead of 101.

It is thus apparent that a synergistic effect occurs between the components since the theoretical RON, calculated from the following values:

| Oligomerizate RON | 95.5 |
|---|---|
| Alkylate RON | 94.5 |
| MTBE | 115 | is only 98.2.

The carburant mixture obtained according to the invention has a specific gravity at 20° C. of 0.710 which is typical of a light gasoline; with respect to distillation, its initial point is 40° C., 10% is distilled at 55° C., 50% at 80° C., 90% at 113° C. and its final distillation point is 188° C.

The present process may be used with $C_3/C_4$ olefinic fractions having another origin than catalytic cracking, for example with coking $C_3/C_4$ cuts.

| | | | | COMPOSITION (WEIGHT PER TIME UNIT) | | | | | | |
|---|---|---|---|---|---|---|---|---|---|---|
| | Initial charge (line 1) | $C_3$ cut (line 3) | $C_4$ cut (line 9) | Stabilized oligomerizate (line 8) | Fresh methanol (line 11) | Recycled methanol (line 12) | MTBE (line 16) | Water (line 17) | Isobutane cut (line 23) | Stabilized alkylate (line 27) | Final gasoline (line 28) |
| Propylene | 15.0 | 15.0 | | | | | | | | | |

-continued

| | Initial charge (line 1) | C₃ cut (line 3) | C₄ cut (line 9) | Stabilized oligomerizate (line 8) | Fresh methanol (line 11) | Recycled methanol (line 12) | MTBE (line 16) | Water (line 17) | Isobutane cut (line 23) | Stabilized alkylate (line 27) | Final gasoline (line 28) |
|---|---|---|---|---|---|---|---|---|---|---|---|
| COMPOSITION (WEIGHT PER TIME UNIT) | | | | | | | | | | | |
| Propane | 5.0 | 5.0 | | | | | | | | | |
| Isobutane | 14.0 | | 14.0 | | | | | | 2.1 | | |
| Isobutene | 6.4 | | 6.4 | | | | | | | | |
| 1-butene | 4.0 | | 4.0 | | | | | | | | |
| 2-butenes | 10.8 | | 10.8 | | | | | | | | |
| n-butane | 4.8 | | 4.8 | | | | | | 2.9 | | |
| Oligomerizate | | | | 14.8 | | | | | | | |
| Methanol | | | | | 3.5 | 0.3 | | | | | |
| MTBE | | | | | | | 9.6 | | | | |
| Alkylate | | | | | | | | | | 30.9 | |
| Total gasoline (40–188° C.) | | | | | | | | | | | 55.3 |
| Water | | | | | | | | 4 | | | |

What is claimed is:

1. A process for producing a blended high octane gasoline, comprising the steps of:
   (a) oligomerizing an olefinic C₃ cut comprising propylene, and recovering an oligomerizate boiling in the gasoline range;
   (b) contacting a mixture of methanol and an olefinic C₄ cut comprising isobutene, isobutane and at least one n-butene with an acid catalyst under isobutene etherification conditions to produce methyl tert.-butyl ether and unreacted C₄ hydrocarbons;
   (c) fractionating the effluent from step (b) and separately recovering a methyl tert.-butyl ether fraction and an unreacted C₄ hydrocarbon fraction comprising said at least one n-butene;
   (d) subjecting the unreacted C₄ hydrocarbon fraction from step (c) to aliphatic alkylation conditions, and recovering an alkylate boiling in the gasoline range; and
   (e) blending at least a portion of said oligomerizate with at least a portion of said methyl tert.-butyl ether fraction and at least a portion of said alkylate, and recovering a blended high octane gasoline.

2. A process according to claim 1 wherein the C₃ cut used in step (a) and the C₄ cut used in step (b) are each produced by fractional distillation of a C₃/C₄ catalytic cracking cut.

3. A process according to claim 1, wherein the oligomerization in step (a) is effected in the presence of a catalyst obtained by contacting a group IV to VIII metal compound with an alkylaluminum compound.

4. A process according to claim 3, wherein the alkylaluminum compound is a hydrocarbylaluminum halide and the metal compound is a nickel compound.

5. A process according to claim 1, wherein the etherification reaction between the C₄ cut and methanol is effected in the presence of a sulfonated resin.

6. A process according to claim 1, wherein the alkylation in step (d) is effected in the presence of hydrofluoric acid.

7. A process according to claim 1, wherein the isobutane/C₄ olefins ratio in the unreacted C₄ hydrocarbon fraction from step (c) is lower than 1, and isobutane is added to increase this ratio to at least 1 in the feed to step (d).

8. A process according to claim 2, wherein said C₃/C₄ catalytic cracking cut has the following composition, by weight:

| | |
|---|---|
| propylene | 15–35% |
| isobutane | 15–30% |
| isobutene | 5–15% |
| 1-butene | 3–10% |
| 2-butenes | 10–25% |
| propane + n-butane | 8–30% |

9. A process according to claim 1, wherein the C₃ art used in step (a) and the C₄ cut used in step (b) have the following respective compositions, by weight:

| C₃ cut | C₄ cut |
|---|---|
| propane:15–50% | n-butane:5–20% |
| propylene:50–85% | isobutane:20–50% |
| | isobutene:10–25% |
| | 1-butene:5–15% |
| | 2-butene:10–40% |

* * * * *